US005185008A

United States Patent [19]

Lavender

[11] Patent Number: 5,185,008
[45] Date of Patent: Feb. 9, 1993

[54] TWO-PIECE OSTOMY APPLIANCE AND COUPLING THEREFOR WITH ROCKING WEDGE LOCK

[75] Inventor: Michael R. Lavender, Round Lake Beach, Ill.

[73] Assignee: Hollister Incorporated, Libertyville, Ill.

[21] Appl. No.: 719,157

[22] Filed: Jun. 21, 1991

[51] Int. Cl.$^5$ .............................................. A61F 5/44
[52] U.S. Cl. ...................................... 604/338; 604/342
[58] Field of Search .............................. 604/332–345; 220/354, 465

[56] References Cited

U.S. PATENT DOCUMENTS

| 2,833,324 | 5/1958 | Burroughs | 150/0.5 |
|---|---|---|---|
| 2,901,098 | 8/1959 | Tupper | 206/46 |
| 3,090,526 | 5/1963 | Hamilton et al | 222/105 |
| 3,131,870 | 5/1964 | Henchert | 239/567 |
| 3,165,227 | 1/1965 | Crowell et al. | 220/42 |
| 3,446,391 | 5/1969 | Yates | 220/60 |
| 3,515,306 | 6/1970 | Roper et al. | 220/60 |
| 3,566,946 | 3/1971 | MacDonald | 220/60 |
| 3,572,413 | 3/1971 | Livingstone | 150/0.5 |
| 3,603,485 | 9/1971 | Vivier | 222/129 |
| 3,732,909 | 5/1973 | Rooke et al. | 150/0.5 |
| 4,335,827 | 6/1982 | Knize et al. | 220/284 |
| 4,359,051 | 11/1982 | Oczkowski | 128/283 |
| 4,419,100 | 12/1983 | Alexander | 604/339 |
| 4,460,363 | 7/1984 | Steer et al. | 604/336 |
| 4,520,943 | 6/1985 | Nielsen | 220/281 |
| 4,640,435 | 2/1987 | Dutt | 220/307 |
| 4,775,373 | 10/1988 | Steer | 604/338 |
| 4,786,285 | 11/1988 | Jambor | 604/342 |
| 4,828,553 | 5/1989 | Nielsen | 604/339 |
| 4,872,869 | 10/1989 | Johns | 604/342 |
| 4,931,045 | 6/1990 | Steer | 604/338 |

OTHER PUBLICATIONS

Alexander U.S. patent application Ser. No. 358,639, filed Mar. 16, 1982, abandoned but identified in U.S. Pat. No. 4,419,100.
Hollister Two–Piece Ostomy System with Floating Flange, 1982 (commercial literature).
Two–Piece Ostomy System Drainable Pouches, 1982 (commercial literature.)

Primary Examiner—Randall L. Green
Assistant Examiner—R. Clarke
Attorney, Agent, or Firm—Tilton Fallon Lungmus

[57] ABSTRACT

A two-piece ostomy appliance having a pair of coupling rings that detachably connect a collection pouch and an adhesive faceplate. One of the coupling rings, preferably the faceplate coupling ring, is provided with a substantially non-compressible insert that includes an axially-extending collar, a bulbous non-deformable wedge body, and a radially-extending pivot stem that centrally connects the collar and wedge body. The pivot stem allows limited forward and rearward rocking movement of the wedge body about a pivot axis extending through the stem. A massive front portion of the wedge body has an inwardly and rearwardly curved bearing surface of progressively increasing distance from the pivot axis so that the radial width of the insert decreases as the wedge body rocks rearwardly and forceably increases as it rocks forwardly about the axis, in response to frictional engagement with the walls of the channel, when coupling and uncoupling forces are exerted on the rings.

21 Claims, 3 Drawing Sheets

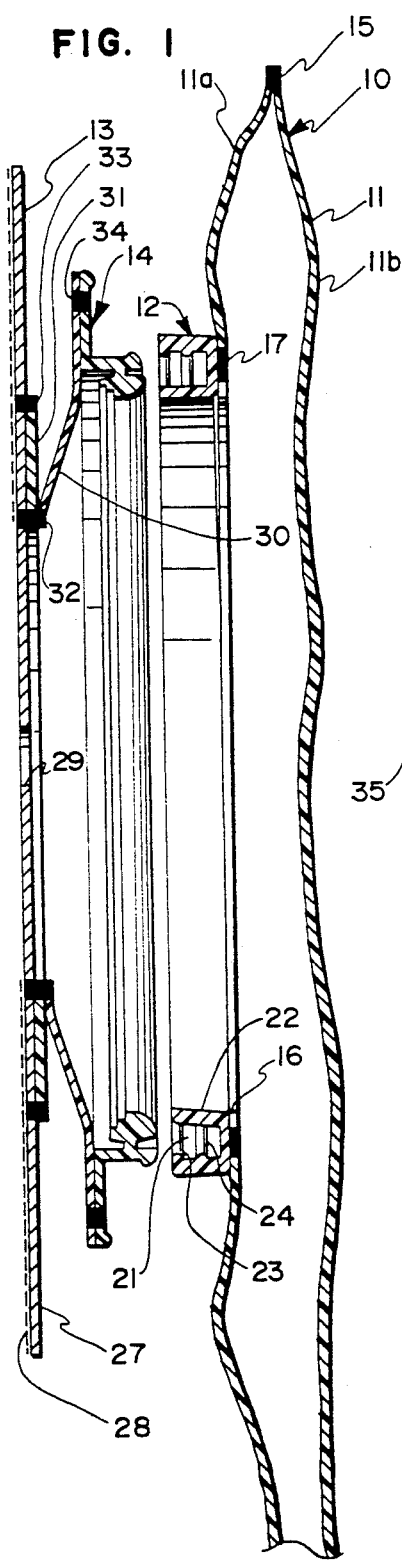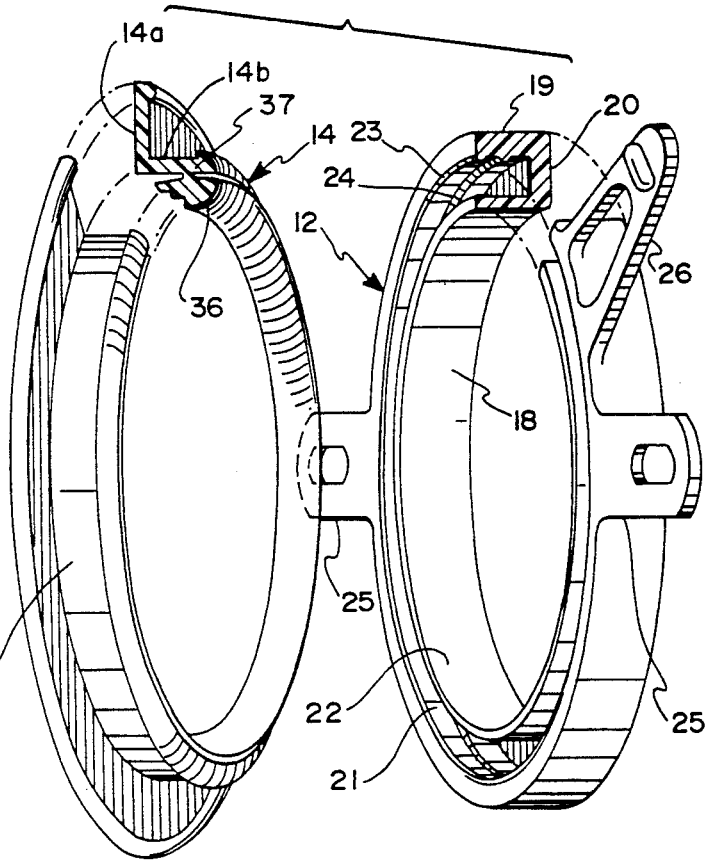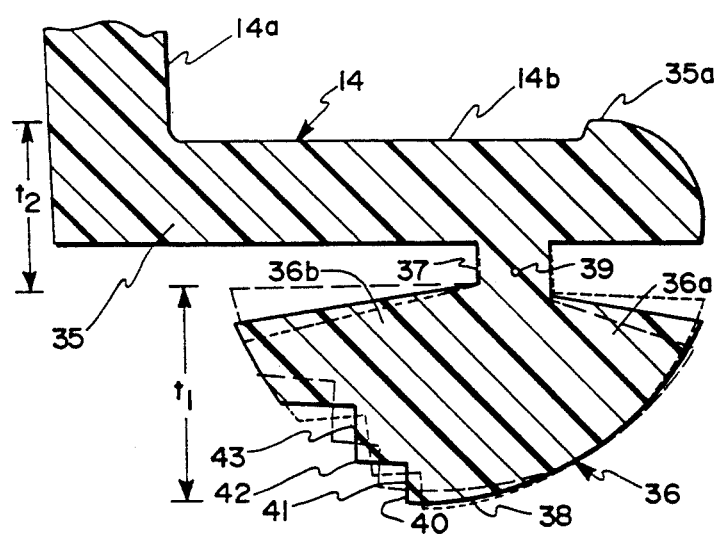

TWO-PIECE OSTOMY APPLIANCE AND COUPLING THEREFOR WITH ROCKING WEDGE LOCK

BACKGROUND AND SUMMARY

One widely-available two-piece ostomy appliance (Hollister Two-Piece Ostomy System) includes a collection pouch having a channel-defining coupling ring extending about an opening in a wall of the pouch and an adhesive faceplate having a mating ring with a compressible insert portion receivable in the channel. The insert portion includes a relatively thick and rigid annular member having a tapered, deformable wiper flange that angles rearwardly and away from the front end of the annular member for resiliently and sealingly engaging one of the walls of the channel when the parts are coupled together. The opposite wall of the channel is provided with at least one bead engagable with an opposing bead projecting from the side of the annular member opposite from the deformable wiper flange. Since the width of the insert in an uncompressed state is greater than that of the channel, simultaneous latching on the bead side of the annular member and fluid-tight sealing on the wiper flange side occur when the coupling rings are fitted together.

To insure a secure fluid-tight coupling of the rings, both the compressible insert with its thin wiper flange and the walls of the channel become deformed when the parts are connected. The wiper flange is flexed towards the thick annular member to which it is integrally joined at the same time the side walls of the channel are spread outwardly so that such walls diverge in the direction of the channel entrance. One result of such coaction and the divergence of the channel walls is that the tightness of the fit between the parts will progressively diminish whenever the insert is shifted towards the channel entrance. As the tension and deformation of both the channel and the flexible wiper flange are reduced, the security of the latch and the tightness of the seal are compromised.

It is a further characteristic of such a two-piece construction that if the coupling rings are dimensioned to provide a tighter interfit and insure greater security against accidental detachment of the rings, the effort required to join the rings together is also increased. Security of attachment is therefore achieved at the expense of requiring substantial deformation of the parts during assembly, with such deformation necessitating the application of substantial coupling forces that some users, especially the elderly and infirm, may have difficulty providing.

A main aspect of this invention therefore lies in providing a two-piece ostomy appliance with coupling rings that provide a high level of security when mated together but still require relatively little effort for a user to assemble. High security is achieved because of the expansive rocking action of a non-deformable wedge body that occurs during the initial stages of ring separation. Such rocking movement effectively increases the radial width of the substantially non-compressible insert and thereby increases the resistance to ring separation. At the same time, ease of assembly is promoted because the reverse rotation of the non-deformable wedge body during a coupling operation decreases the effective width of the insert, thereby lessening deformation of the channel and reducing the force needed to urge the insert into that channel.

These results, and the differences in the manner of operation responsible for them, may be achieved by substituting only the male coupling ring (e.g., the faceplate ring) of this invention for the standard male ring of the conventional two-piece system as described above. The standard channel-providing ring (e.g., the pouch ring) may remain unchanged, although modifications of that ring may be made if desired.

Unlike prior faceplate coupling rings, the faceplate ring of this invention has an annular insert that is substantially non-compressible in radial directions and includes an axially-extending annular collar, a bulbous non-deformable wedge body of toroidal shape, and an annular radially-extending pivot stem that connects the non-deformable wedge body and the collar in concentric relation. The wedge body has a massive front portion that projects forwardly beyond the stem and a similarly massive rear portion that extends rearwardly behind the stem. A bearing surface that is provided by the front portion (also, if desired, by part of the rear portion) curves inwardly and rearwardly at progressively increasing distances from the pivot axis extending through the stem. Because of the progressively increasing radii of curvature in a rearward direction and the provision of a stem which supports the wedge body for limited rocking movement about a pivot axis, the massive non-deformable body functions as a rocking wedge that forceably increases the radial width of the non-compressible insert when the wedge body rocks forwardly and decreases such width when the wedge rocks rearwardly. Rearward rocking action occurs during insertion and forward rocking action during extraction, so the locking action is self-augmenting, automatically adjusting to reduce coupling forces during assembly while providing forceful expansion and desirably high resistance to accidental separation of the parts when they are fully connected.

Other features, advantages, and objects will appear from the specification and drawings.

DRAWINGS

FIG. 1 is a vertical sectional view illustrating an ostomy appliance embodying this invention and illustrating the parts in uncoupled condition.

FIG. 2 is an enlarged exploded view of the coupling rings with sections removed therefrom to illustrate the cross sectional configuration of the parts.

FIG. 3 is a greatly enlarged fragmentary cross sectional view of the faceplate coupling ring illustrating the range of rocking movement of the wedge-like body and the dimensional changes associated with such movement.

DETAILED DESCRIPTION OF PREFERRED EMBODIMENTS

Figure 4:
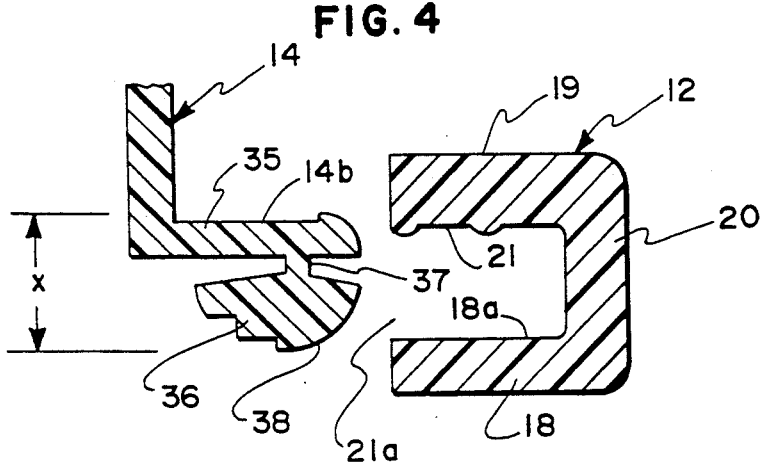
FIGS. 4–6 are somewhat schematic sectional views depicting the rings in separated condition (FIG. 4) and fully assembled condition (FIG. 5) and also showing the rocking and wedging actions that occur during the initial stages of ring separation (FIG. 6).

Referring to FIGS. 1-6 of the drawings, the numeral 10 generally designates a two-piece ostomy appliance, one piece constituting a collection pouch 11 with a first coupling ring 12 and the other comprising a faceplate 13 equipped with a second coupling ring 14. As shown, pouch 11 and ring 12 are entirely conventional, being of the type marketed by Hollister Incorporated, Libertyville, Ill., for coaction with a faceplate coupling ring substantially different in structure and mode of operation than illustrated ring 14. Therefore, some features of the pouch ring 12 as shown may be unnecessary or of reduced significance in the present context.

Pouch 11 is formed of two sheets 11a and 11b of thermoplastic material heat-sealed together along their edges 15. The pouch may be provided with a drain outlet at its lower end which may be closable by a suitable clamping device (not shown), such as the one disclosed in U.S. Pat. No. 3,523,534, or it may be sealed at its lower end, effectively rendering the pouch "non-drainable." One wall 11a of the pouch has a side opening 16 with the first coupling ring 12 concentrically heat-sealed at 17 to the outer surface of the pouch wall 11a about that opening.

Pouch ring 12 is channel-shaped in cross section, having a pair of inner and outer side walls 18 and 19 joined by a connecting wall 20. The annular channel defined by the ring 12 faces in an axial direction away from pouch 11. Opening 22 of the ring aligns with the stoma opening 16 of the pouch. The channel-side surface 18a of the inner wall 18 is smooth and substantially cylindrical (when the ring 12 is in an untensioned state as shown in FIGS. 1 and 2), and one or more annular beads or ribs 23, 24 may be provided along the opposing channel-side surface of outer wall 19. If desired, the outer wall may also have outwardly-projecting apertured ears 25 for attachment to a suitable belt for additional security, all as well known in the art. A tab 26 extends outwardly from outer wall 19 (FIG. 2) to assist a user in uncoupling the rings when removal of a pouch is desired.

Except for the distinctive second coupling ring 14, faceplate 13 is of known construction. The faceplate may include a highly-flexible panel or plate 27 preferably formed of a gas-penetrable but water-resistant microporous material. Various materials having such properties are known and may be used. The panel is coated on its back or rear side with a medical-grade pressure-sensitive adhesive schematically represented by dashed line 28 so that the faceplate may be adhesively secured to a patient's peristomal skin surface.

Panel 27 is provided with a small central opening 29 that serves as a starter opening in which a user may insert the blade of a pair of scissors to cut an opening in the faceplate of a size and outline that matches a patient's stoma. Alternatively, the product as supplied to the user may be provided with a central opening sized to fit his/her stoma.

The second coupling ring 14 may be secured to panel 13 in any suitable manner. A preferred construction is depicted in FIG. 1 where a thin, flexible annular web 30 is sealed along its outer perimeter to ring 14 and along its inner perimeter to a highly-flexible thermoplastic intermediate ring 31. The intermediate ring is in turn heat sealed along inner and outer concentric heat seal zones 32 and 33 to the microporous panel 27. For details of such a construction and its advantages, reference may be had to co-owned U.S. Pat. Nos. 4,419,100 and 4,213,358. It may be noted, however, that while the "floating flange" feature disclosed in U.S. Pat. No. 4,419,100 has substantial advantages when used with prior two-piece appliances, those advantages may be less important when used with a two-piece system having the distinctive coupling ring 14 as shown and described herein. Thus, in the construction shown and described herein, the omission of web 30 and the direct connection of ring 14 to panel 13 (or to intermediate ring 31) may be less significant than if such changes were made in a more conventional two-piece coupling ring system.

Referring in particular to FIGS. 2 and 3, the faceplate coupling ring 14 is integrally formed of a semi-rigid thermoplastic material such as low-density polyethylene, a material that may also be used for pouch ring 12. The faceplate ring includes a planar or radially-extending flange portion 14a and an axially-extending insert portion 14b. The rear face of the flange portion is connected by heat seal 34 to the outer edge of annular web 30, and the integral insert portion 14b extends forwardly from the circular inner periphery of flange portion 14a.

As shown most clearly in FIGS. 2 and 3, the annular insert portion 14b comprising an axially-extending cylindrical collar 35 having a bead 35a, a bulbous non-deformable wedge body 36 of toroidal shape, and an annular, radially-extending pivot stem 37. The stem is integrally formed with the collar and wedge body and connects the two in concentric relation, with the stem being generally centrally disposed in relation to the wedge body.

The wedge body 36 includes a massive front portion extending forwardly beyond the stem 37 and a similarly massive rear portion 36b projecting rearwardly behind the stem. The relatively large mass of the wedge body 36 is important in rendering that body substantially non-deformable in use. As shown in FIG. 3, the radial thickness $t_1$ of the toroidal wedge body 36 is far greater than the radial thickness of collar 35, or of pivot stem 37, or of both the collar and pivot stem combined ($t_2$).

The pivot stem 37 supports the wedge body so that front portion 36a and rear portion 36b are spaced radially from the collar 35. As depicted in FIG. 3, the front portion 36a has an inwardly and rearwardly curved bearing surface 38 of progressively increasing distance from a pivot axis 39 located in or at stem 37. Stated differently, the radius of curvature of surface 38 measured from pivot axis 39 increases gradually and progressively as the surface curves rearwardly from the forward limits of front portion 36a. In the particular embodiment depicted in FIGS. 1-6, the curved bearing surface 38 continues rearwardly and radially inwardly to an annular edge 40 along rear portion surface 38 and of the wedge body as a whole.

Edge 40 is defined in part by a step 41 and, although an abrupt change in direction is depicted (edge 40 is shown to be defined by surfaces meeting at approximately right angles), it is believed that an edge or transition defined by surfaces meeting at more of an obtuse angle might also be suitable. Furthermore, while a second edge 42 and second step 43 are shown, it is believed that such edge and step rarely come into play during normal operation and, if desired, may even be omitted. (See, for example, the embodiment of FIGS. 7-9.)

Figure 5:
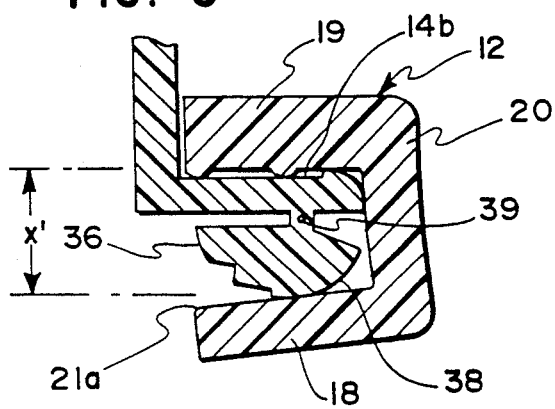
Figure 6:
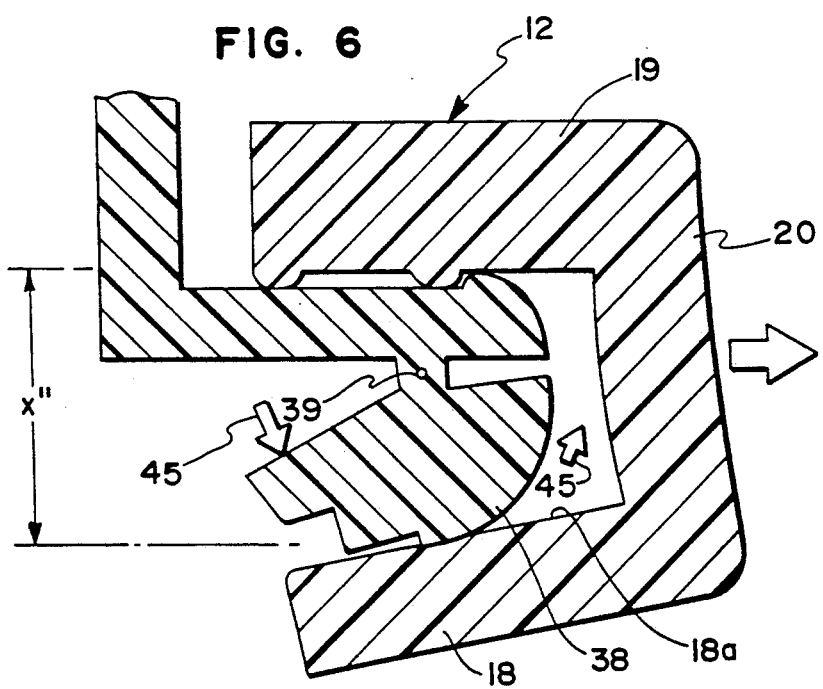

Referring to FIGS. 4–6, the radial width of insert 14b exceeds the radial width of the channel 21 provided by pouch coupling ring 12 when that ring is in an untensioned state (FIG. 4). While the semi-rigid plastic material from which the parts are formed permits pivotal action of the stem, insert portion 14b as a whole is substantially non-compressible in a radial direction. Consequently, when the insert portion is forced into channel 21, the pouch ring 12 must flex so that its side walls 18 and 19 are spread outwardly, diverging in the direction of the mouth 21a of channel 21, as shown in FIG. 5.

Of particular importance is the fact that during such insertion, the arcuate bearing surface 38 of wedge body 36 frictionally contacts the smooth surface 18a of inner wall 18, causing the bulbous, non-deformable wedge body 36 to pivot rearwardly (clockwise, in FIG. 5) about axis 39. Since the radius of curvature of surface 38, measured from pivot axis 39, increases in a rearward direction and diminishes in a forward direction, such rearward rocking movement of the non-deformable wedge body effectively reduces the radial thickness of the insert portion. Consequently, if x represents the radial thickness of the non-compressible insert portion 14b when the parts are uncoupled (FIG. 4), the radial dimension x' when the rings are fully joined is significantly less because of the rearward rocking action of the wedge body 36 (FIG. 5). The effect is that the walls 18, 19 of the channel are spread apart a distance significantly less than would be necessary if the non-deformable wedge body 36 were incapable of rocking rearwardly about the pivot axis extending through stem 39.

While the insert portion automatically reduces its radial thickness during insertion into channel 21 to limit the spreading of the channel walls, an opposite effect occurs during extraction. During the initial stages of ring separation, the frictional contact between the curved bearing surface 38 of the wedge body and the surface 18a of channel wall 18 causes the wedge body to rock in a forward direction about pivot axis 39 (FIG. 6). Such forward pivotal movement (counterclockwise, as represented by arrows 45 in FIG. 6) increases the radial thickness of the non-compressible insert member to x", forcing the walls of the channel 18 and 19 further apart and thereby increasing the clamping force exerted by those walls on the insert member. Therefore, unlike prior ostomy couplings, a pivotal action of the non-compressible insert portion of one ring forces the panel walls of the other ring to spread even further apart during ring separation, producing a wedging action that provides increased security against accidental separation of the parts. Despite the relatively high forces required for such accidental separation, the forces needed to join the parts together are relatively low, compared with prior constructions, because of the rearward width-reducing rocking action of the wedge body during insertion.

The extent of rocking action between the extremes depicted in the drawings may be varied considerably depending on factors such as the radius of curvature of surface 38 and the dimensions of the rings. In general, however, it is believed that the extent of such rocking action between the width-reducing condition of insertion and the jamming or wedging condition described should be within the range of about 2 to 20 degrees.

The forces required for intentional separation of the coupling rings are acceptably low notwithstanding the high resistance to accidental separation. During intentional removal of a pouch, a user usually grips tab 26 and pulls it forwardly away from faceplate ring 14 to cause a widening of the channel 21 in the vicinity of the tab and to commence a peeling apart operation that progresses circumferentially about the rings until they are fully separated. The following data are believed indicative of the forces for coupling, unintentional uncoupling, and intentional uncoupling of a ostomy appliance embodying this invention when compared with a standard Hollister Two-Piece system as currently marketed:

| Type of Appliance | Extent of Channel Spreading when Rings are Coupled | Opening Force at 0° (Security) | Opening Force at 30° (Removal) |
|---|---|---|---|
| Standard Hollister Two-Piece System | .035" | 28.7 lb. | 3.8 lb. |
| System Embodying this Invention | .016" | 23.7 lb. | 4.5 lb. |

Both of the appliances represented in this chart used identical pouch rings with channels having a width of 0.108 inches in untensioned (i.e., uncoupled) condition. When the rings of each pair were fully assembled, the channel width for the pouch ring of the standard Hollister Two-Piece System increased to 0.143 inches, or a total increase of 0.035 inches (32.4%), whereas for the coupling embodying this invention, the channel width increased to 124 inches, or an increase of only 0.016 inches (14.8%). The spreading of a channel for a coupling embodying this invention is therefore found to be less than half that for the standard Hollister Two-Piece System. Since identical channel rings were used for both systems, the substantial difference in channel spread between the two is believed to be a reliable indication that the forces necessary to join coupling rings embodying this invention are considerably less than those required for the standard Hollister Two-Piece System.

The second column sets forth the forces required to pull apart pairs of couplings rings when the rings of each pair are maintained in parallel relation (i.e., at zero degree planar difference) and the separation forces are applied normal to the plane of such rings. The resistance to separation under such conditions is considered indicative of the resistance of the couplings to accidental separation under actual conditions of use associated with patient body movement, contact with other objects, etc. The standard Hollister Two-Piece system, at 28.7 pounds, is noted for its high resistance to accidental separation and, at 23.7 pounds, a coupling embodying this invention also offers remarkably high security, especially in view of its relative ease of assembly.

The third column indicates the force needed for intentional separation of the rings when tab 26 of the channel ring for each pair is pulled at an angle of 30 degrees to commence an unpeeling of the rings. Although the opening force of 4.5 pounds for a coupling embodying this invention is higher than that of a standard Hollister Two-Piece coupling (at 3.8 pounds), both are believed to be quite acceptable. Therefore, the data indicate that when used with the same type of channel ring intended for a standard Hollister Two-Piece System, the faceplate coupling ring 14 of this invention with its distinctive rocking wedge construction provides a high level of security against accidental detachment while at the same time requiring considerably lower forces for joining the parts together.

Figure 7:
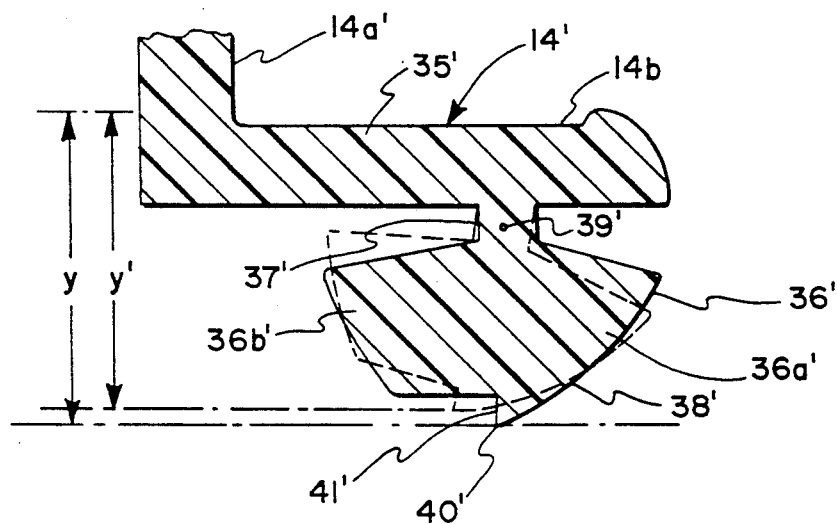
FIG. 7 is an enlarged fragmentary cross sectional view similar to FIG. 3 but depicting a second embodiment of this invention.
Figure 8:
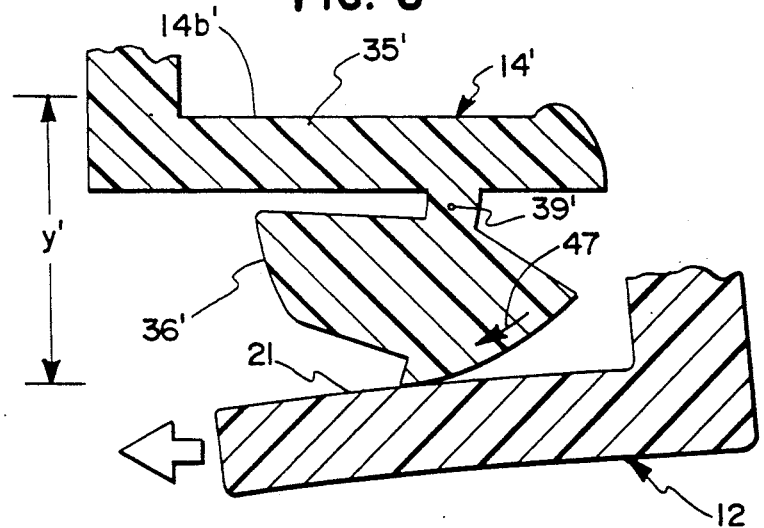
FIG. 8 is a sectional view showing the cooperative relationship of the faceplate ring of FIG. 7 with a pouch coupling ring as such rings are being urged together.
Figure 9:
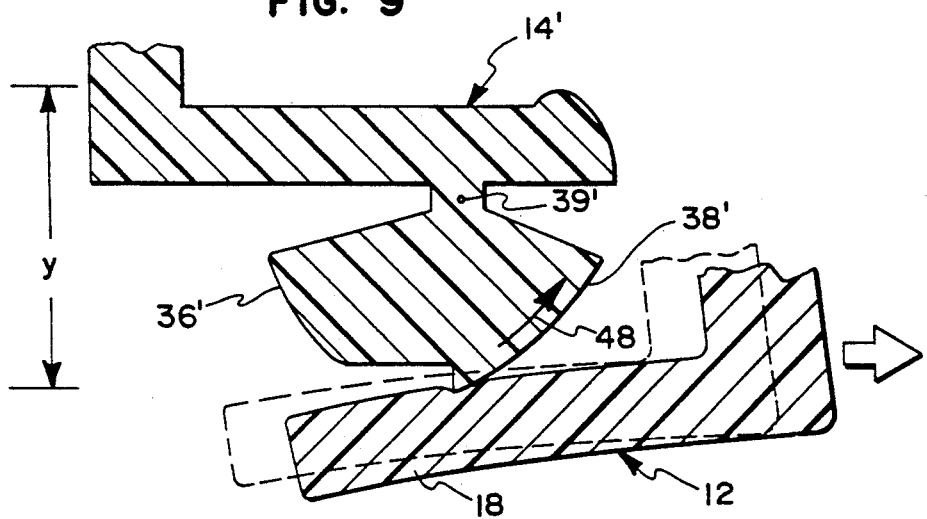
FIG. 9 is a sectional view similar to FIG. 8 but showing the automatic rocking and wedging action that occurs as axial forces are exerted to commence separation of the two rings.

The embodiment of FIGS. 7-9 is similar to the one already described except that wedge body 36' has a bearing surface 38' terminating at an edge 40' that is colinear with pivot stem 37'. Also, only a single step 41' is provided. Collar 35' and pivot stem 37' are like those previously described and in other respects the coupling ring 14' is the same as ring 14 of the preceding embodiment.

The rocking wedge 36' is shown in solid lines in FIG. 7 in its untensioned or unstressed condition—that is, the condition in which it would exist when rings 14' and 12 are uncoupled. The dashed lines depict the rocking wedge 36' in a position it would be expected to assume if ring 14' were coupled with channel ring 12 as previously shown and described. It will be observed that when the non-deformable wedge body 36' is rocked rearwardly about pivot axis 39', as it would be during insertion of the insert portion 14b' into a channel 21, the radial width of the insert portion decreases from dimension y to dimension y'. Such reduction in width occurs despite the fact that, as before, insert portion 14b' is substantially non-compressible; that is, radial forces colinear with stem 37' of a magnitude expected to be encountered in normal operation of the device would not result in any appreciable reduction in dimension y.

When the insert portion 14b' of ring 14' is inserted into the channel 21 of coupling ring 12, as schematically depicted in FIG. 8, the frictional resistance causes wedge body 36' to pivot rearwardly about pivot axis 39' in the clockwise direction represented by arrow 47. The radial dimension of insert 14b' therefore automatically decreases to y' as the wedge body 36' rocks rearwardly. As previously described, such rearward rocking movement results in less spreading of channel 21 than would otherwise be required if the non-deformable wedge body 36' were incapable of rearward rocking movement.

During separation of rings 12 and 14', the wedge body 36' rocks forwardly in the direction represented by arrow 48 in FIG. 9. Because the rearwardly curved bearing surface 38' has a curvature of progressively increasing radii from pivot axis 39', such forward rocking movement forces the wall 18 of the channel outwardly as illustrated, thereby spreading the channel and increasing the resistance to separation of the rings.

While the action of the rocking wedge body 36 has been described as a pivoting about axis 39, it will be understood that axis 39 is circular and the wedge body is toroidal. As the torous-shaped wedge body 36 rotates about axis 39, front and rear portions 36a, 36b of the body must alternately expand or contract circumferentially, depending on the direction of such rotation. The extent of such alternate perimetric expansion/contraction is extremely small and is resisted by the large masses of material of the wedge body 36 located in front of and behind the pivot axis (i.e., portions 36a and 36b). The resistance of the massive front and rear portions 36a and 36b to such change is believed to contribute significantly to the effectiveness of this invention.

In both embodiments, the channel-providing ring 12 has been shown and described as being connected to a pouch and the insert-providing ring 14, 14' as being joined to a faceplate, but it will be understood by those skilled in the art that, if desired, the relationship might be reversed. Other features of the invention have been shown and described in considerable detail for purposes of illustration, but it will be understood that such details may be varied without departing from the spirit and scope of the invention.

I claim:

1. A two-piece ostomy appliance comprising a collection pouch and adhesive faceplate means for peristomal attachment to a patient; said pouch having a stoma-receiving opening and a first coupling ring secured thereto about said opening; said first coupling ring having a pair of spaced concentric side walls and a connecting wall capable of being flexed to define an expandable annular channel facing axially away from said pouch; and a second coupling ring having annular insert means receivable in said expandable channel for sealing and locking engagement with said first ring; wherein the improvement comprises said annular insert means being substantially non-compressible and frictionally engagable with both of said side walls; said insert means including an axially-extending annular collar, a bulbous non-deformable body of toroidal shape, and an annular radially-extending pivot stem connecting said non-deformable body and annular collar in concentric relation; said body including a front portion projecting forwardly beyond said stem toward said pouch and a rear portion extending rearwardly beyond said stem away from said pouch, with both said front and rear portions being spaced radially from said collar; said stem supporting said body for limited forward and rearward rocking movement about a pivot axis at said stem; said front portion of said body having a rearwardly curved bearing surface of progressively increasing distance from said pivot axis; whereby, the width of said non-compressible insert means decreases as said non-deformable body rocks rearwardly and increases as said body rocks forwardly about said pivot axis, in response to frictional engagement with a wall of said channel, when coupling and uncoupling forces, respectively, are applied to said rings.

2. The appliance of claim 1 in which said curved bearing surface extends rearwardly beyond said front portion and terminates at a force-concentrating contact edge along said rear portion.

3. The appliance of claim 1 in which said curved bearing surface terminates at the rear end of said front portion at a force-concentrating contact edge radially aligned with said pivot stem when said second coupling ring is untensioned.

4. The appliance of claims 2 or 3 in which a step is provided by said bulbous non-deformable body at said contact edge; said contact edge being engagable with a surface of one of said side walls within said channel.

5. The appliance of claim 4 in which said surface of said one side wall is smooth and generally cylindrical when said channel is unexpanded.

6. The appliance of claim 4 in which said step is defined by surfaces meeting at generally right angles.

7. The appliance of claim 1 in which said bulbous non-deformable is supported by said pivot stem for rocking movement falling within the range of about 2 to 20 degrees about said pivot axis.

8. The appliance of claim 1 in which the maximum radial thickness of said bulbous non-deformable body substantially exceeds the maximum radial thickness of said collar.

9. The appliance of claim 8 in which said maximum radial thickness of said bulbous non-deformable body exceeds the combined maximum radial thickness of both said collar and said stem.

10. The appliance of claim 1 in which said bulbous non-deformable body is disposed radially inwardly of said collar.

11. The appliance of claim 1 in which said collar, pivot stem, and rocking bulbous non-deformable body are formed integrally of semi-rigid plastic material.

12. A coupling ring for a two-piece ostomy appliance; said ring being joined to a first component of said two-piece appliance consisting of either a faceplate or a pouch and including substantially non-compressible insert means for insertion into an axial channel of a mating coupling ring joined to a second component of said two-piece appliance; said insert means including an axially-extending annular collar, a bulbous non-deformable body of toroidal shape, and an annular pivot stem connecting said body and collar in radially-spaced concentric relation; said bulbous body including a front portion projecting forwardly beyond said stem away from said first component and a rear portion extending rearwardly beyond said stem toward said first component; said stem supporting said body for limited forward and rearward rocking movement about a pivot axis; and said front portion of said body having a rearwardly curved bearing surface of progressively-increasing distance from said pivot axis.

13. The coupling ring of claim 12 in which said curved bearing surface extends rearwardly beyond said front portion and terminates at a force-concentrating contact edge along said rear portion.

14. The coupling ring of claim 12 in which said curved bearing surface terminates at the rear end of said front portion at a force-concentrating contact edge radially aligned with said pivot stem when said second coupling ring is untensioned.

15. The coupling ring of claims 13 or 14 in which a step is provided by said bulbous non-deformable body at said contact edge.

16. The coupling ring of claim 15 in which said step is defined by surfaces meeting generally at right angles.

17. The coupling ring of claim 12 in which said bulbous non-deformable body is supported by said pivot stem for rocking movement falling within the range of about 2 to 20 degrees about said pivot axis.

18. The coupling ring of claim 12 in which the maximum radial thickness of said bulbous non-deformable body substantially exceeds the maximum radial thickness of said collar.

19. The coupling ring of claim 18 in which said maximum radial thickness of said bulbous non-deformable body exceeds the combined maximum radial thickness of both said collar and said stem.

20. The coupling ring of claim 12 in which said bulbous non-deformable body is disposed radially inwardly of said collar.

21. The coupling ring of claim 12 in which said collar, pivot stem, and rocking bulbous non-deformable body are formed integrally of semi-rigid plastic material.

* * * * *